US00PP19873P3

(12) United States Plant Patent
Richer

(10) Patent No.: US PP19,873 P3
(45) Date of Patent: Mar. 31, 2009

(54) ROSE PLANT NAMED 'EMILY CARR'

(50) Latin Name: ***Rosa* sp.**
Varietal Denomination: Emily Carr

(75) Inventor: Claude Richer, Quebec (CA)

(73) Assignee: Her Majesty The Queen in right of Canada, as represented by the Minister of Agriculture and Agri Food, Saint-Jean-sur-Richelieu, Quebec (CA)

( * ) Notice: Subject to any disclaimer, the term of this patent is extended or adjusted under 35 U.S.C. 154(b) by 0 days.

(21) Appl. No.: 11/880,142

(22) Filed: Jul. 19, 2007

(65) Prior Publication Data

US 2009/0038036 P1 Feb. 5, 2009

(51) Int. Cl.
*A01H 5/00* (2006.01)

(52) U.S. Cl. ..... Plt./108
(58) Field of Classification Search ..... Plt./108
See application file for complete search history.

(56) References Cited

PUBLICATIONS

UPOV–ROM GTITM Plant Variety Database Jun. 2007, GTI Jouve Retrieval Software, Citation for Rosa 'Emily Carr', one page.*
Adamson's Heritage Nursery Ltd. Wholesale Catalogue, 2007 (6 pages).
Pepiniere Abbotsford naturellement 2007 ( 5 pages).
Jeffries Nurseries Ltd. 2006/2007 Wholesale Listing (6 pages).
Sanwell Nurseries: 2007 Annual Catalogue ( 6 pages).
Phytoclone 2007 Purchase Order form ( 6 pages).
Candian Artist Series of Roses 2007 Releases ( 3 pages).
Aubin Nurseries Inventory, Jan. 19, 2007 ( 30 pages).
Novaplants Nurseries Liste de Prix 2007 ( 6 pages).

* cited by examiner

*Primary Examiner*—Annette H Para
*Assistant Examiner*—June Hwu
(74) *Attorney, Agent, or Firm*—Klarquist Sparkman, LLP

(57) ABSTRACT

A new and distinct variety of rose, distinguished by its deep red flowers, disease resistance and cold tolerance.

13 Drawing Sheets

Latin name of the genus and species of the plant claimed: *Rosa* sp.
Variety denomination: 'Emily Carr'.

SUMMARY OF THE INVENTION

The present invention relates to a new and distinct variety of rose named 'Emily Carr'. The new rose 'Emily Carr' resulted from a hybridization programme and is a selection from a series of cross by manual pollination. The series can be described as follows:

[(Lammert's selection×Morden Cardinette)×Morden Cardinette]×Cuthbert Grant

The cultivar was created in Morden, Manitoba in 1982, Canada, and selection subsequently occurred at another location in Quebec, Canada in 1998–1999.

The 'Emily Carr' rose plant variety of the present invention: a) is resistant to mildew, b) almost continuous flowering, with deep red flowers, c) the flowers are semi-double, d) the plant is a large shrub with an upright growth habit, and d) shows cold tolerance.

Asexual reproduction of this new variety shows that the foregoing and other characteristics come true to form, are firmly fixed, and are established and transmitted through succeeding propagations. The instant cultivar was asexually reproduced by softwood cutting in Morden, Manitoba, Canada. Cutting size can be variable but new shoots (softwood) taken 3–5 nodes in length root well under intermittent mist, common in the industry. Root hormone (IBA) can speed root development.

BRIEF DESCRIPTION OF THE DRAWINGS

The 'Emily Carr' rose is illustrated by the accompanying colour photographs, in which.

Figure 1A:
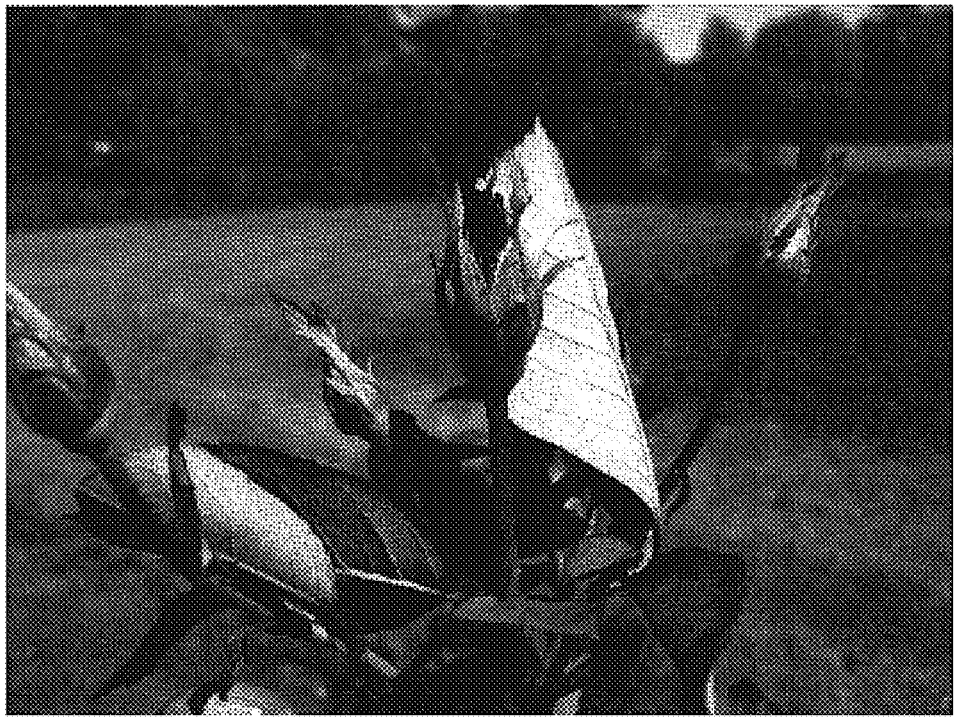
FIGS. 1A–D show 'Emily Carr' flower buds with closed sepals (FIGS. 1A–B) in comparison with flower buds with closed sepals of a reference variety 'Champlain' (unpatented) (FIG. 1C–D)
Figure 1B:
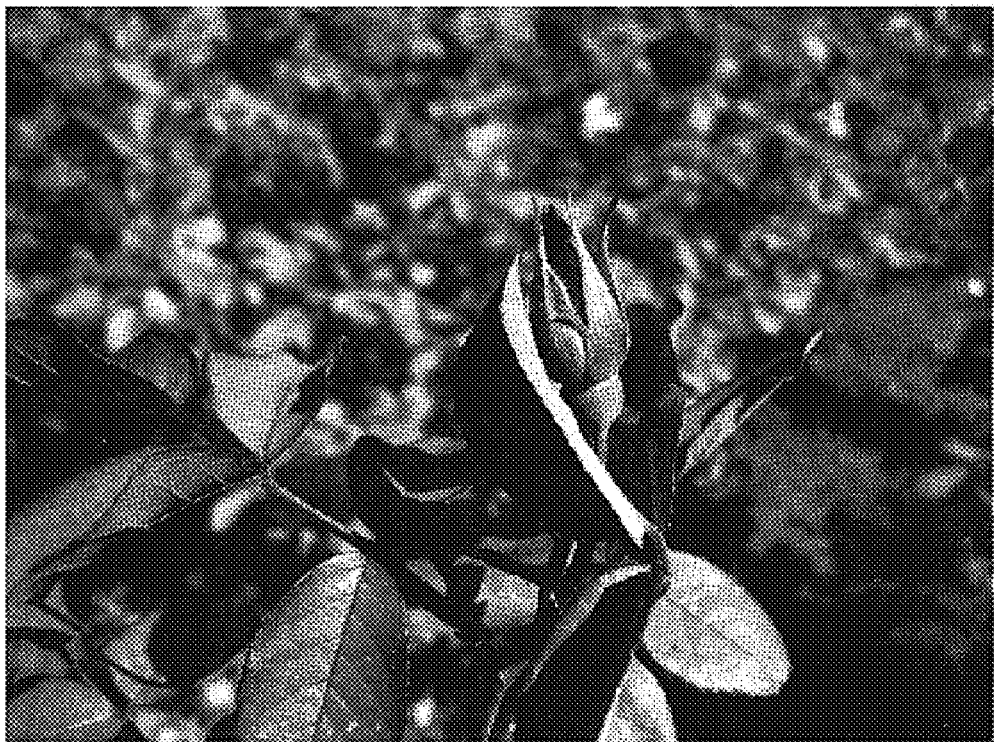
Figure 1C:
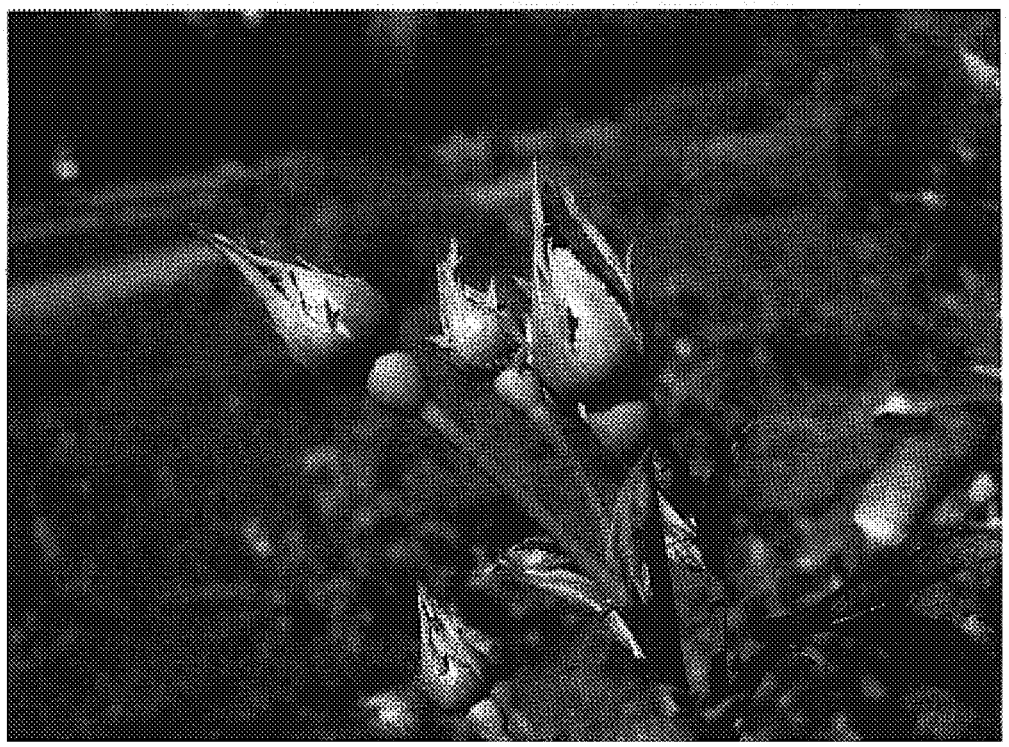
Figure 1D:
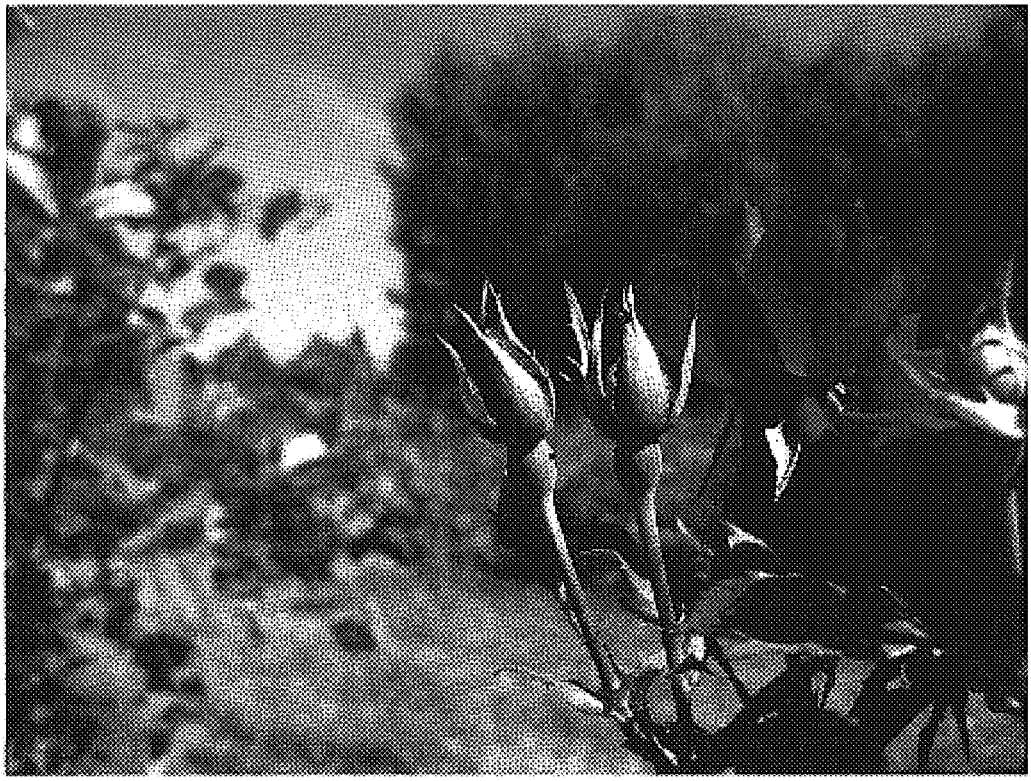
Figure 2A:
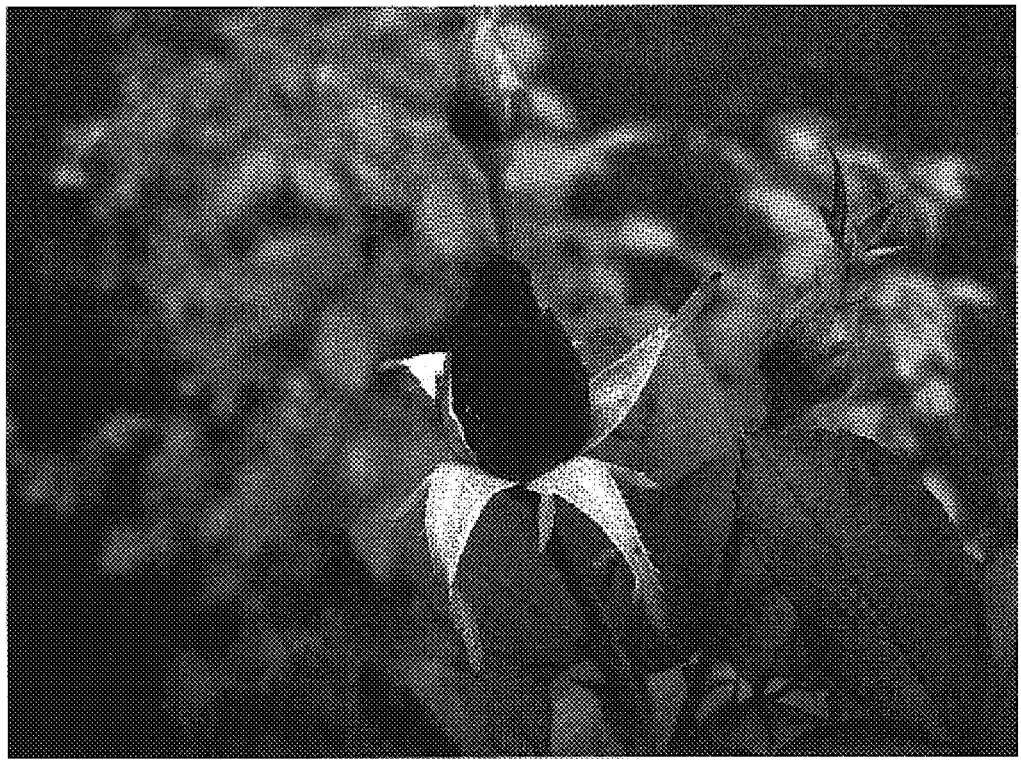
FIGS. 2A–B show an 'Emily Carr' flower bud with opening sepals (FIG. 2A) in comparison with a flower bud with opening sepals of a reference variety 'Champlain' (unpatented) (FIG. 2B)
Figure 2B:
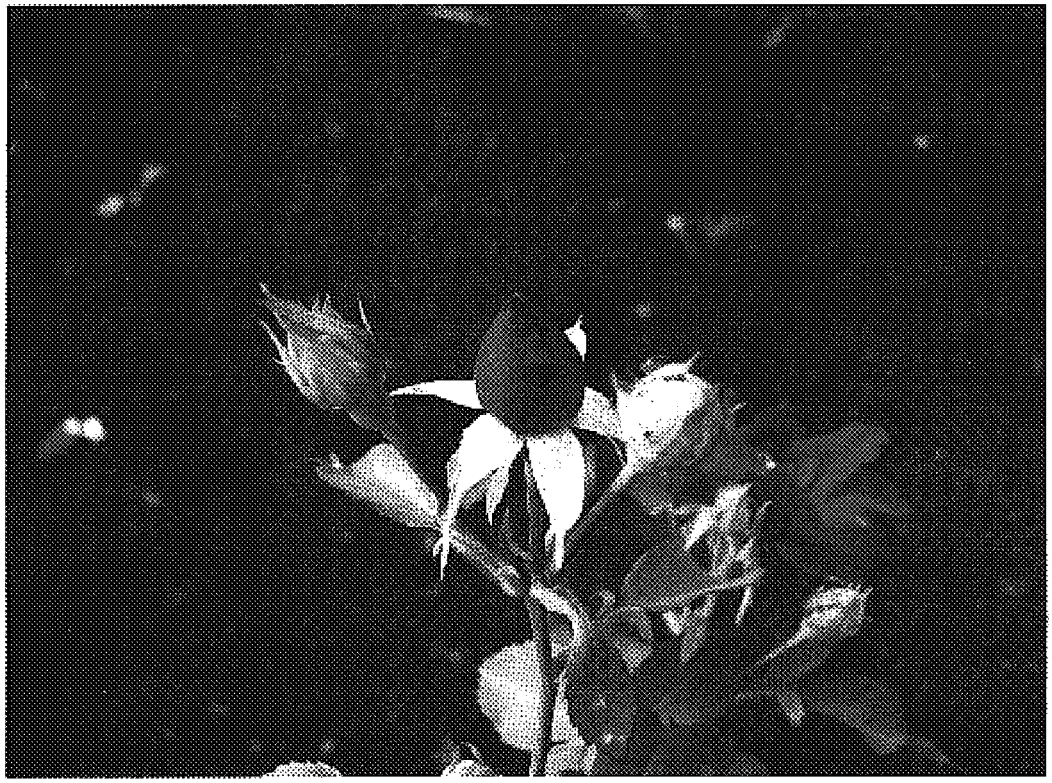
Figure 3A:
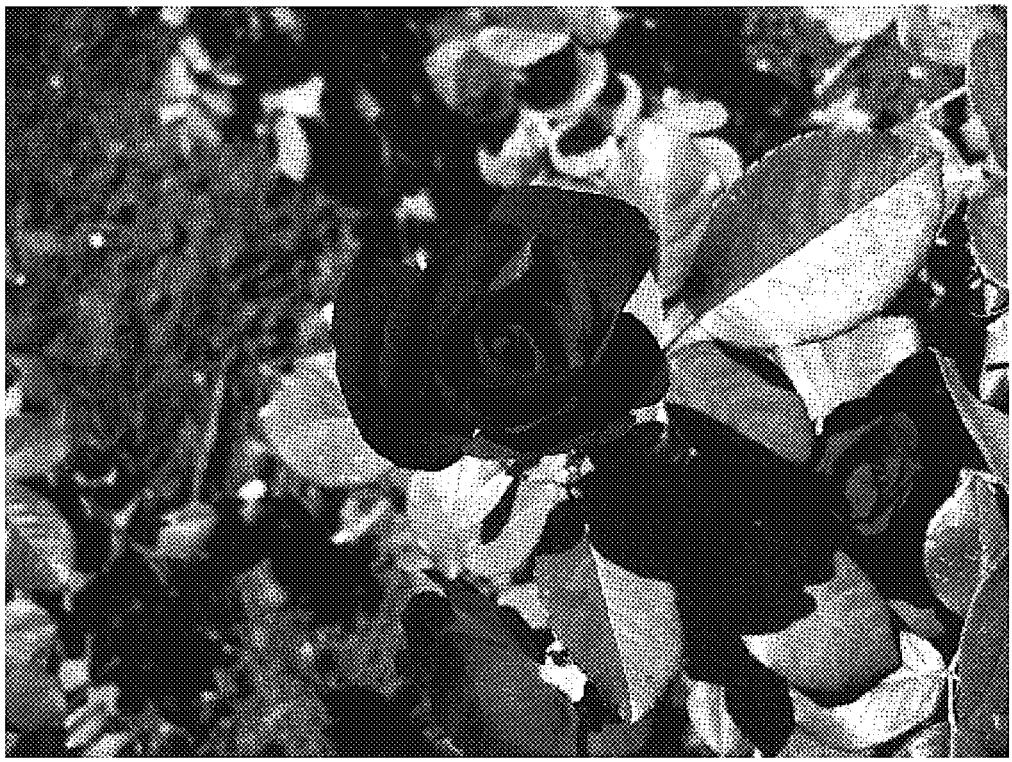
FIGS. 3A–B show an opening 'Emily Carr' flower bud (FIG. 3A) in comparison with an opening flower bud of a reference variety 'Champlain' (unpatented) (FIG. 3B)
Figure 3B:
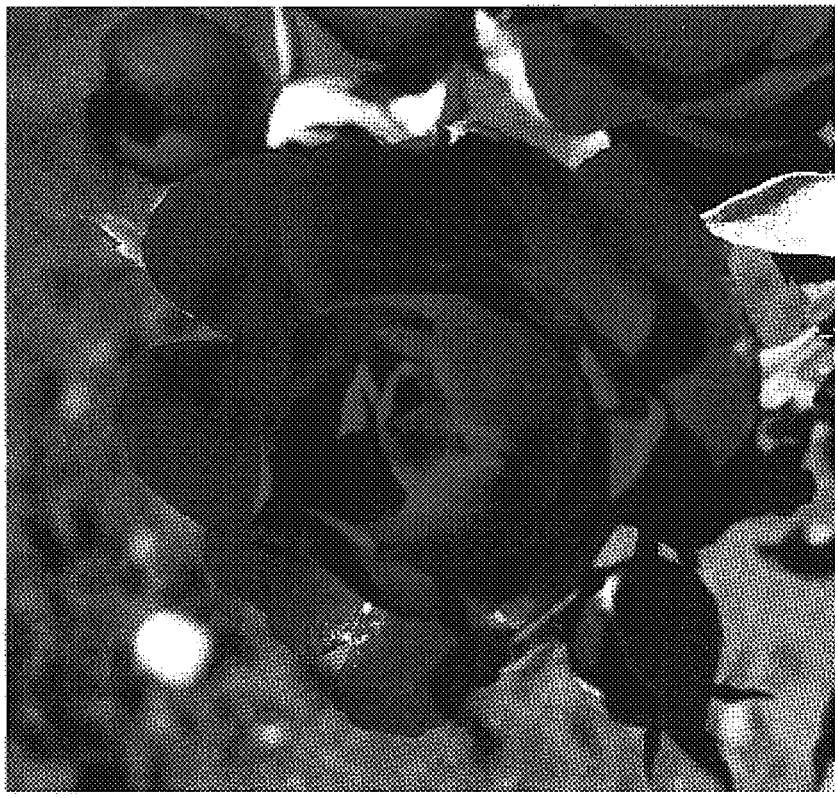
Figure 4A:
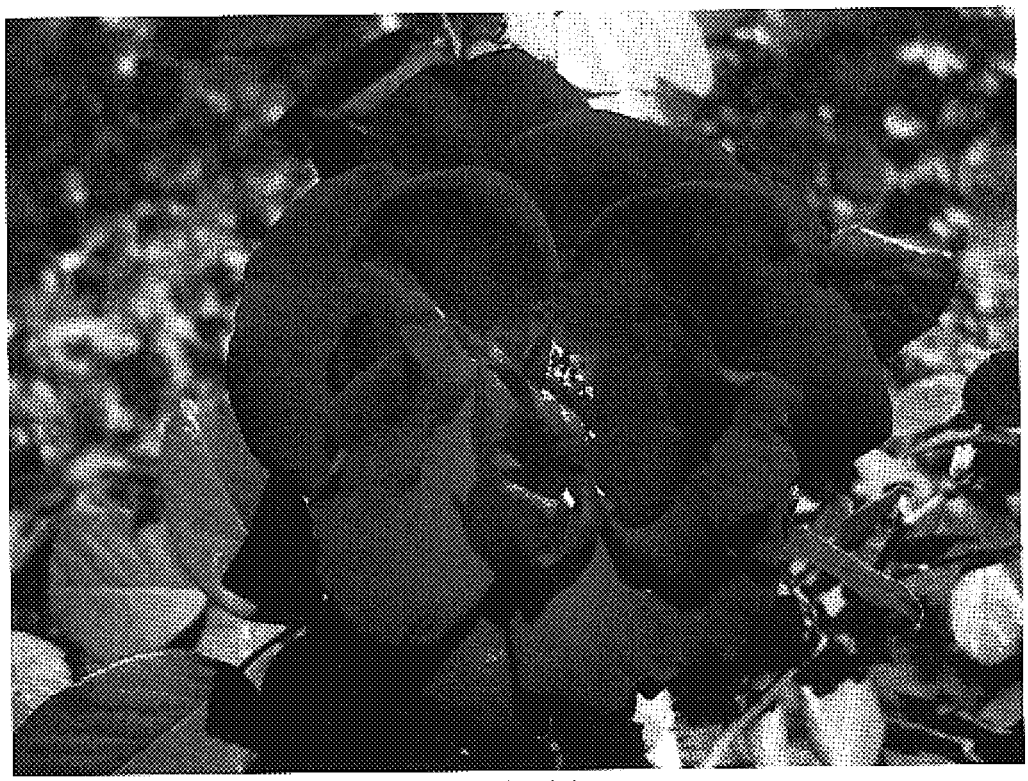
FIGS. 4A–B show an 'Emily Carr' flower (FIG. 4A) in comparison with a flower of a reference variety 'Champlain' (unpatented) (FIG. 4B)
Figure 4B:
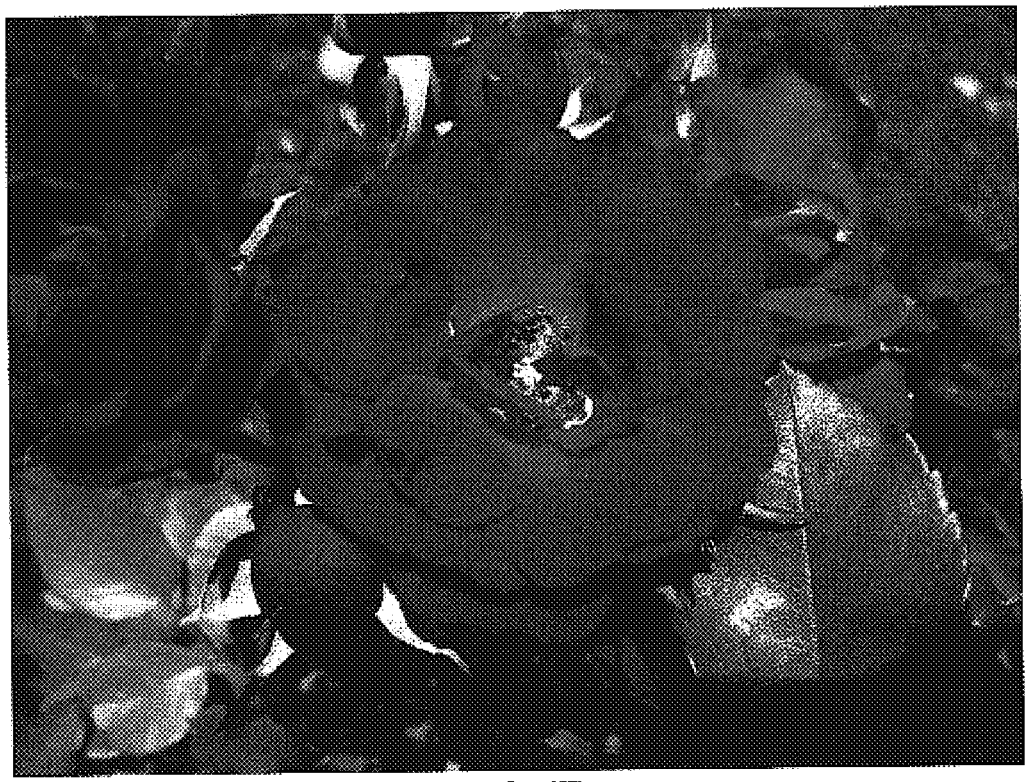
Figure 5A:
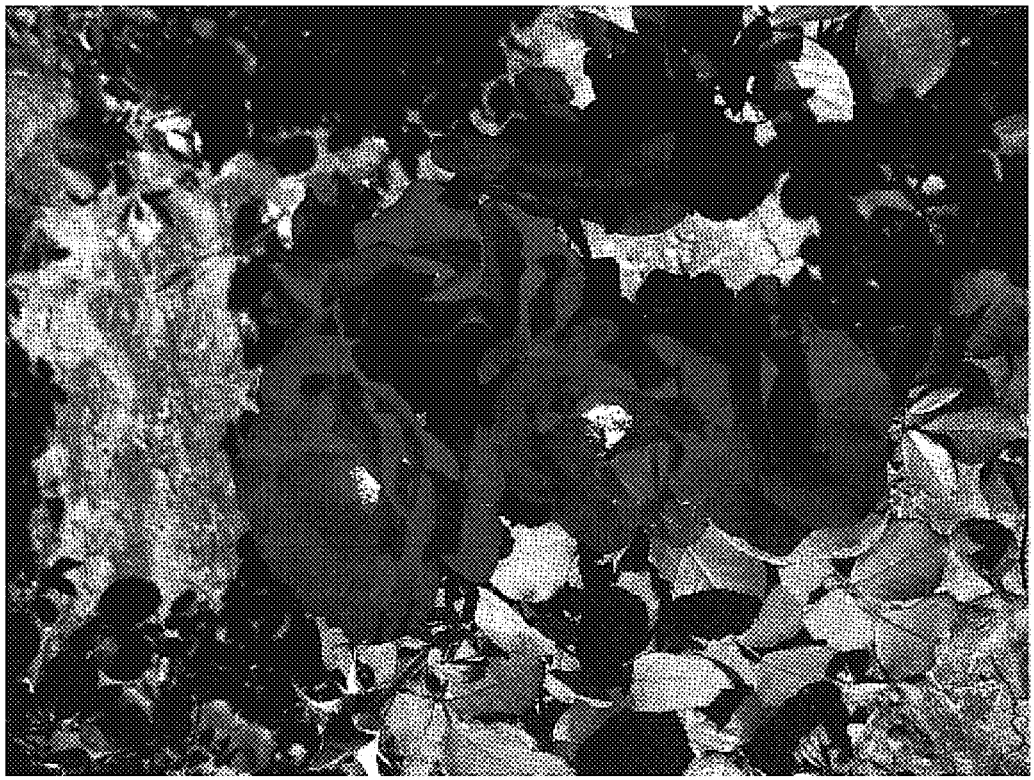
FIGS. 5A–B show an 'Emily Carr' flower cluster (FIG. 5A) in comparison with a flower cluster of a reference variety 'Champlain' (unpatented) (FIG. 5B)
Figure 5B:
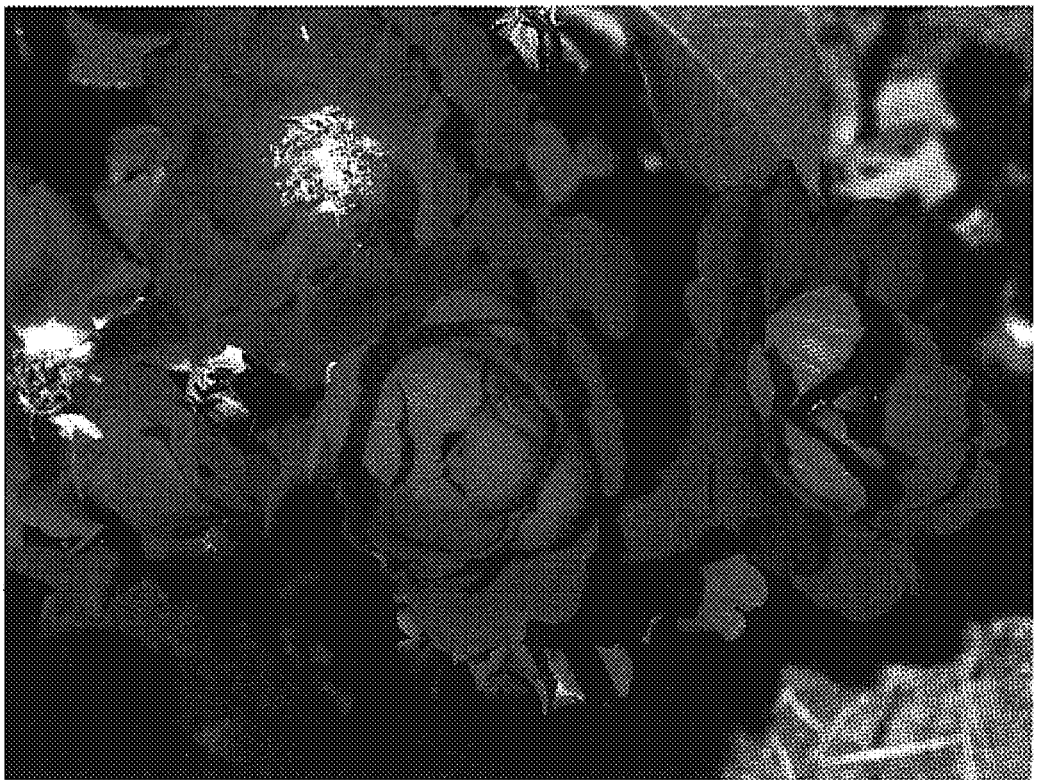
Figure 6A:
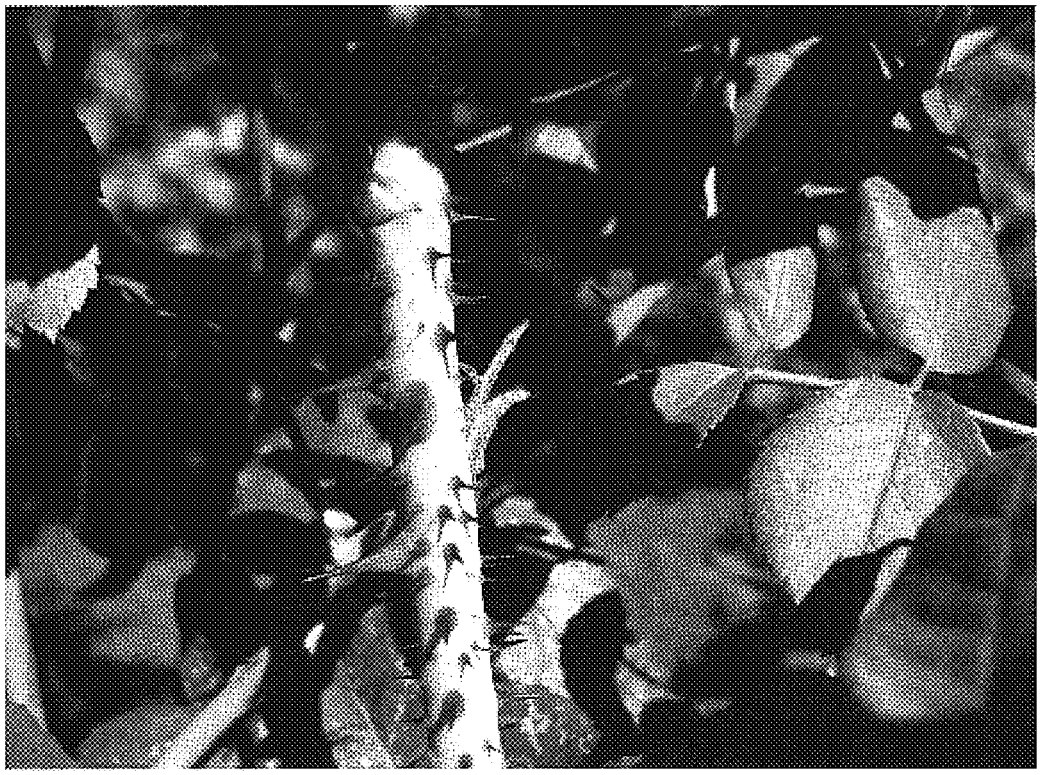
FIGS. 6A–B show 'Emily Carr' stems (FIG. 6A) in comparison with stems of a reference variety 'Champlain' (unpatented) (FIG. 6B)
Figure 6B:
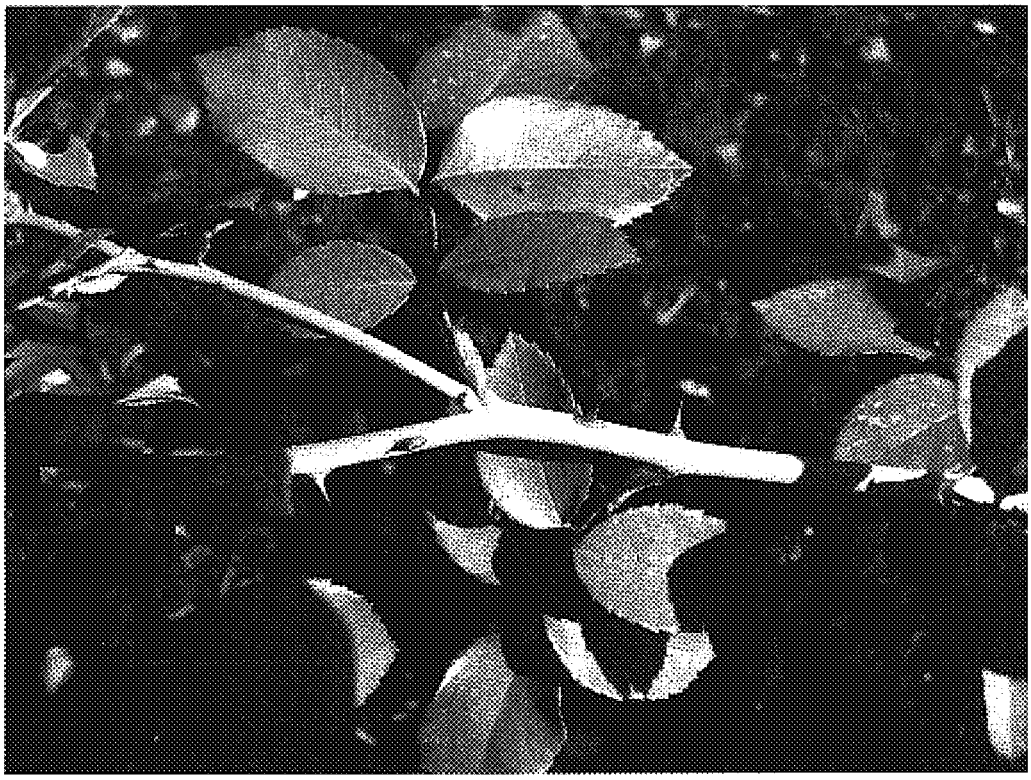
Figure 7A:
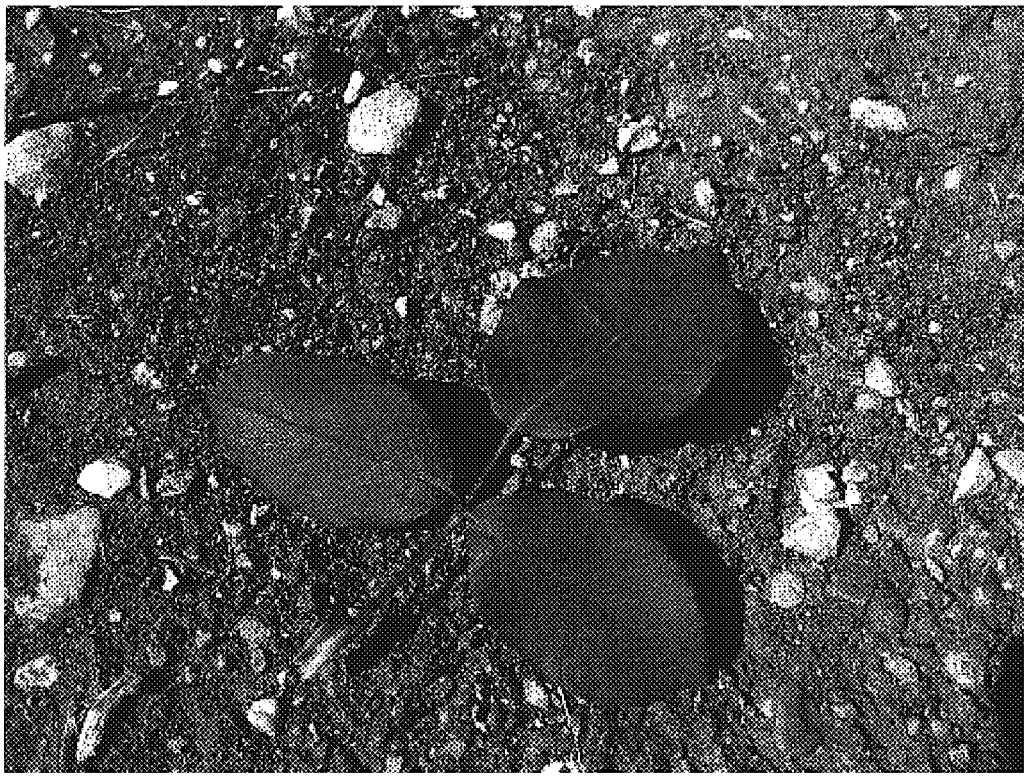
FIGS. 7A–B show an 'Emily Carr' leaf with 3 folioles (FIG. 7A) in comparison with that of a reference variety 'Champlain' (unpatented) (FIG. 7B)
Figure 7B:
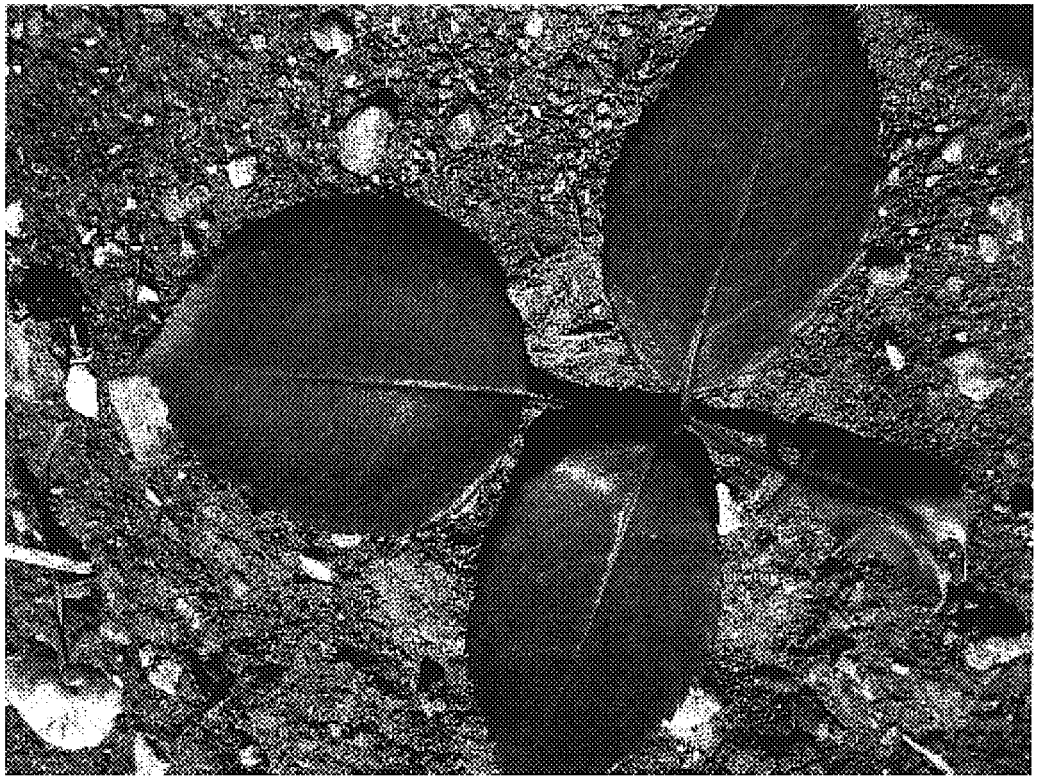
Figure 8A:
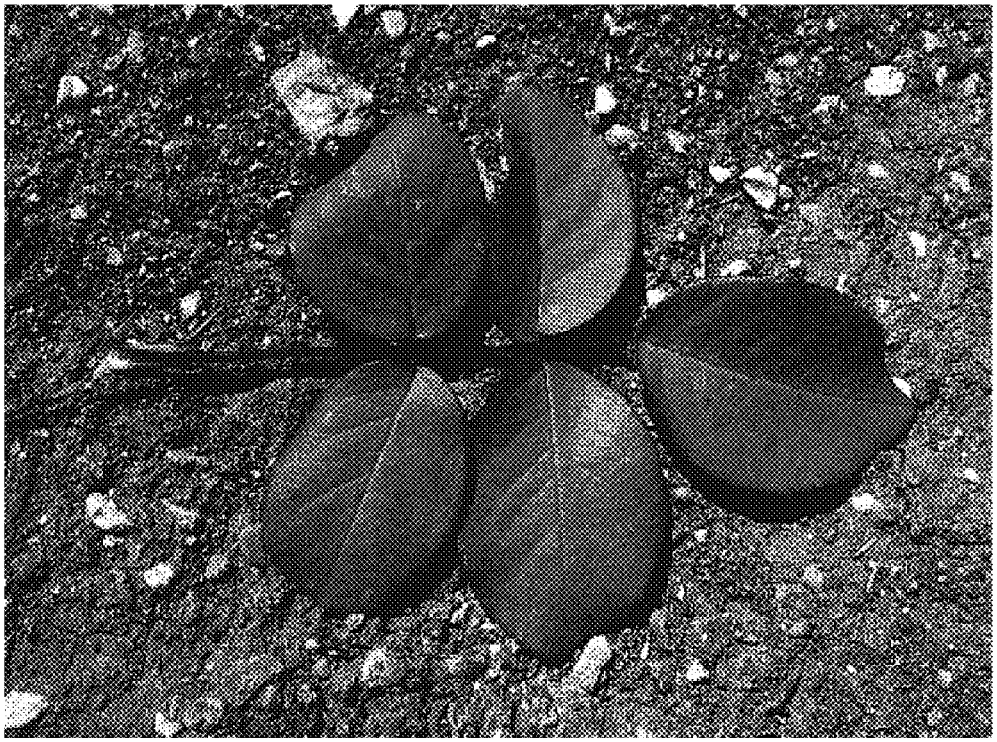
FIGS. 8A–B show an 'Emily Carr' leaf with 5 folioles (FIG. 8A) in comparison with that of a reference variety 'Champlain' (unpatented) (FIG. 8B)
Figure 8B:
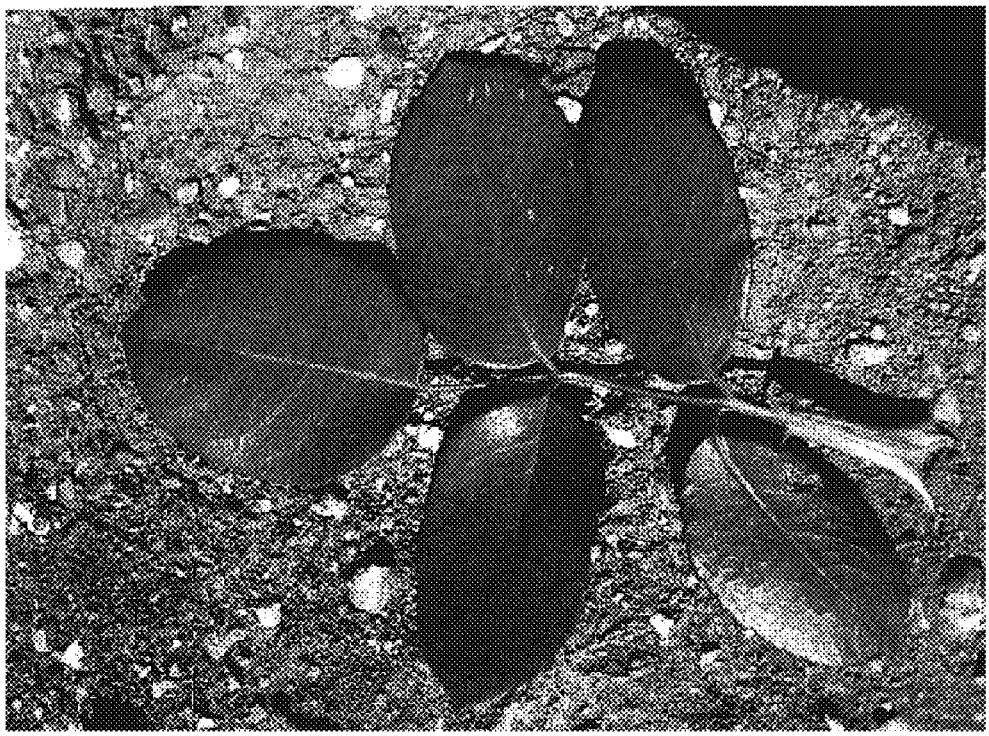
Figure 9A:
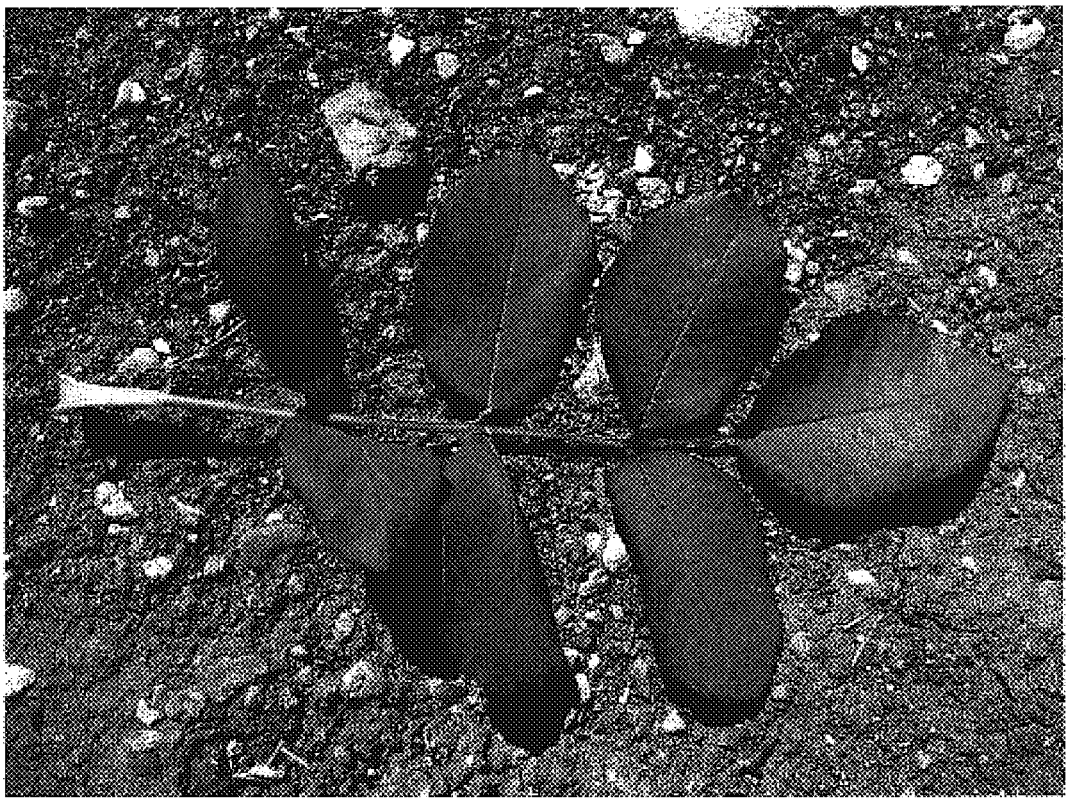
FIGS. 9A–B show an 'Emily Carr' leaf with 7 folioles (FIG. 9A) in comparison with that of a reference variety 'Champlain' (unpatented) (FIG. 9B)
Figure 9B:
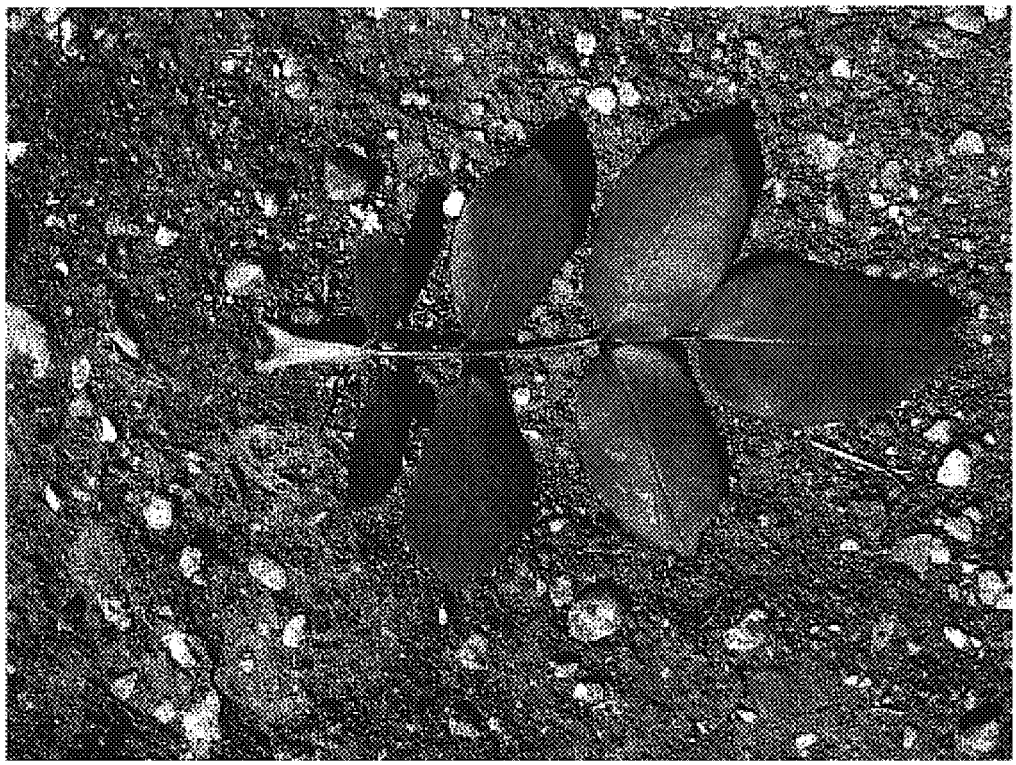
Figure 10A:
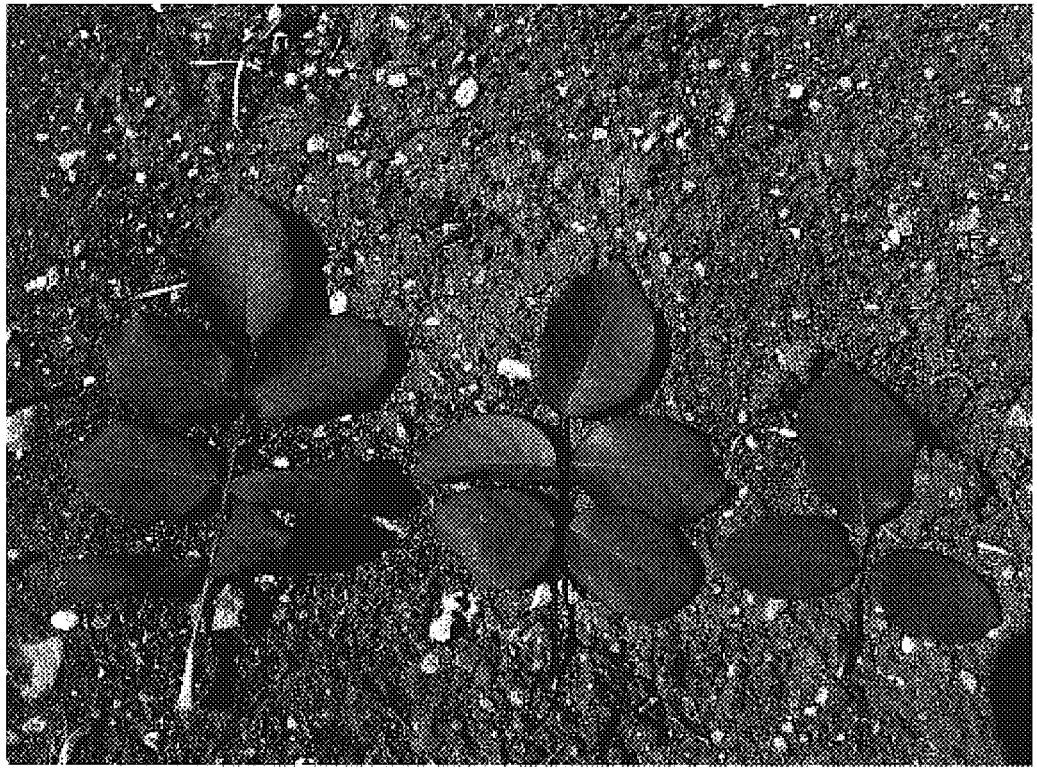
FIGS. 10A–B show 'Emily Carr' leaves (FIG. 10A) in comparison with leaves of a reference variety 'Champlain' (unpatented) (FIG. 10B)
Figure 10B:
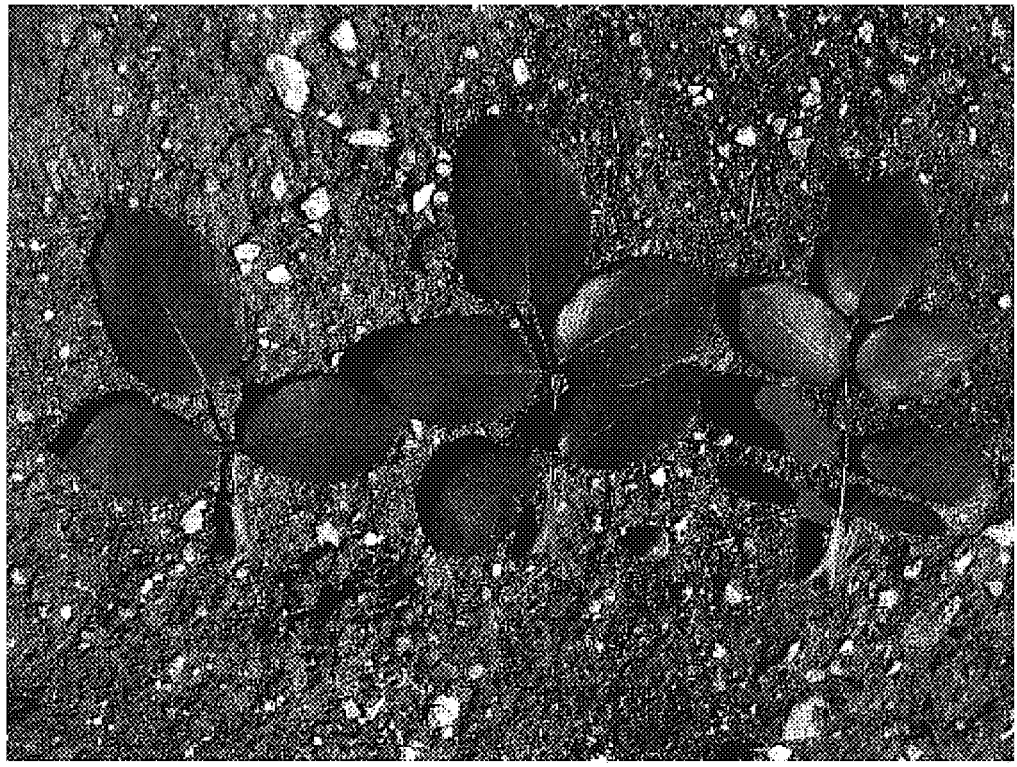
Figure 11A:
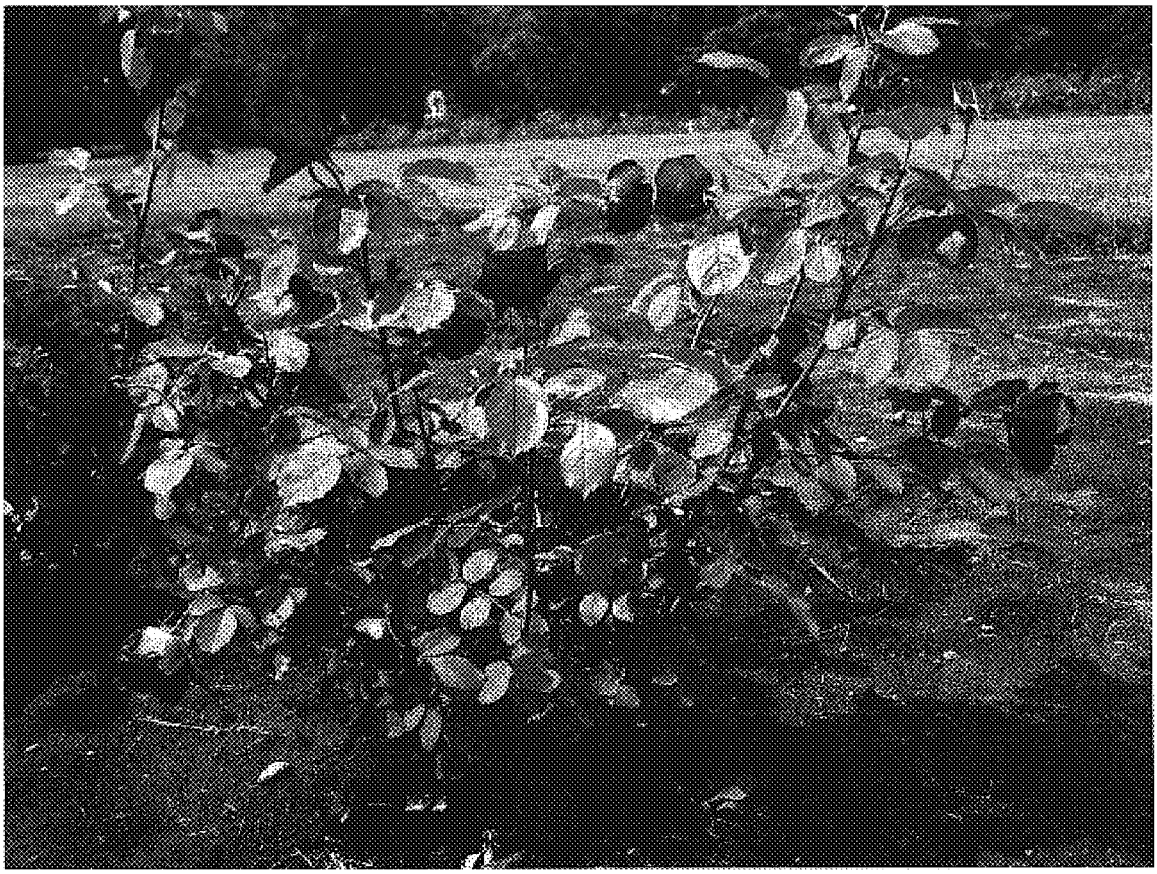
FIGS. 11A–B show an adult 'Emily Carr' plant (FIG. 11A) in comparison with an adult plant of a reference variety 'Champlain' unpatented) (FIG. 11B).
Figure 11B:
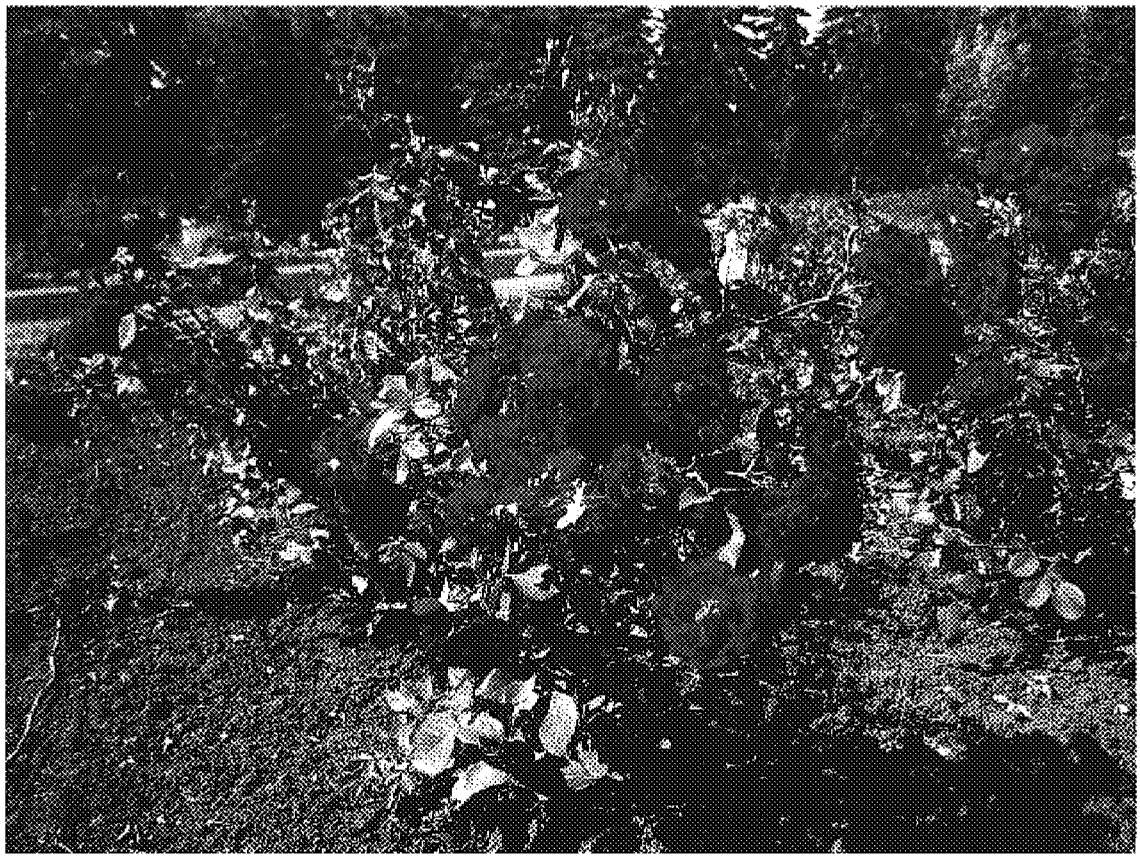

The colours of an illustration of this type may vary with lighting and other conditions under which conditions and, therefore, colour characteristics of this new variety should be determined with reference to the observations described herein, rather than from these illustrations alone.

DETAILED DESCRIPTION

The original variety and progeny have been observed growing in a cultivated area in Quebec, Canada. Certain characteristics of this variety, such as growth and colour, may change with changing environmental conditions (e.g., light, temperature, moisture, nutrient availability, or other factors). Colour descriptions and other terminology are used in accordance with their ordinary dictionary descriptions, unless the context clearly indicates otherwise. Colour designations are made with reference to the Royal Horticultural Society (R.H.S.) Colour Chart. All colour characteristics were determined using the 1986 version of the Royal Horticultural Society (R.H.S.) colour charts and measured characteristics were based on ten plan measurements. It should be understood that the colours may vary, depending on factors such as growing and lighting conditions.

The comparative tests and trials for 'Emily Carr' were conducted in Morden, Manitoba. The plants were placed in groups of 3 with a plant spacing of 3 feet and row spacing of 7 feet. Evaluations were made over 7 years. The plants used in the assessment of the characteristics were planted in 1996 (long beds) and 1991 (NTA) and had reached mature stature when assessed in 2005 and again on Jun. 30, 2008 and on Jul. 11, 2008.

'Emily Carr' can be distinguished from its parents by the following:

The female parent, 'Cardinette' (unpatented) derived selection is a less hardy selection. 'Emily Carr' is more vigorous;

Compared to its male parent, 'Cuthbert Grant' (unpatented), 'Emily Carr' is redder in color, is more up-right and has slightly smaller flowers.

The 'Emily Carr' rose was compared to the 'Champlain' (unpatented) variety, referred to as the "reference variety." For comparison, several physical characteristics of the rose variety 'Champlain' (unpatented) are compared in Chart 1.

CHART 1

| | 'Emily Carr' | 'Champlain' (unpatented) |
|---|---|---|
| Growth type | Large species variety shrub rose | Small explorer shrub rose |
| Flowers per shoot | 7 (mean) | 24 (mean) |
| Flower type | Semi-double | Double |
| General tonality | 53A | 57B-C |
| Petal spot colour (outer) | 61C | 155A and 7A |
| Petal spot colour (inner) | 57A | 15A |

CHART 1-continued

| | 'Emily Carr' | 'Champlain' (unpatented) |
|---|---|---|
| Outer stamen filament | White with green tinge | Orange-red |
| Resistance to mildew | Resistant | Moderately susceptible |
| Stems | Strong upright, stand up better than 'Champlain' (unpatented) | |

Species: *Rosa* 'Emily Carr'.

Plant:

*Height.*—1.25 mm.

*Width.*—1.6 m.

*Habit.*—Upright to bushy.

Commercial classification: Small hardy shrub rose.

Branches:

*Colour.*—Young stems: purple 59A, 183D. Adult stems: 146C.

*Texture.*—The surface texture of the mature stem, yellow-green (RHS 146C) is generally smooth. Thorns are medium to numerous and occasional prickles are present. Immature stems are generally smooth, grey-purple (RHS 183D) with a few immature thorns and prickles.

*Lenticels.*—Grey-brown (RHS 199A).

Thorns:

*Configuration.*—Upper part is deep concave, lower part is concave

*Quantity.*—Long prickles: 10–19 per 10 cm of stem. Short prickles: over 30 per 10 cm of stem.

*Length of long prickles.*—9.7 mm (mean).

*Colour.*—59A for your prickles and 165B for mature prickles.

Leaves:

*Sized.*—Approximately 105–179 mm in length and 85–112 mm in width.

*Colour* (*at first flush*).—Upper surface: 147A. Under surface: 147B.

*Glossiness.*—The upper surface of mature leaves is weak-medium glossiness while the lower surface is not glossy but pubescent along veins.

Leaflets:

*Number.*—7.

*Shape.*—Rounded at base; apex has an acuminate tip.

*Size* (*terminal leaflet*).—Approximately 51–66 mm in length and 42–55 mm in width.

*Indentation of leaf margin* (*terminal leaflet*).—Serrated.

Stipule:

*Size.*—Approximately 23 mm in length with the auricles and 18 mm in length without auricles. Approximately 7 mm in width.

*Color.*—Yellow-green (RHS 146A).

Petiole: Length (26.7 mm) varies with position along the growing stem and growing conditions and soil/media fertility. Generally petiolules average 1.8 mm to 3.6 mm in length.

*Texture.*—Smooth with small prickles and hairs present on the upper surface while the lower surface is smooth, hairy and may have small thorns.

*Color.*—Greyed-purple in the groove (RHS 183B) and yellow-green (RHS 146A).

Inflorescence:

*Flowering.*—Medium.

*Number of flowering periods.*—Almost continuous.

*Length of flowering period.*—Flowering generally occurs in two major flushes, late spring (June) and summer and averages 13 weeks with 10–50% blossoms visible between week 25 and 37.

*Flowers per shoot.*—4–14.

*Rachis.*—Surface texture is smooth with small prickles and hairs present on the upper surface and small thorns, prickles and hairs on the lower surface.

Sepals:

*Length* (*including extensions*).—20–30 mm.

*Configuration.*—Extensions are medium.

Bud:

*Shape.*—Pointed.

*Colour.*—60A upon opening. Upper surface (¼ open): 60A. Under surface (¼ open): 60A.

Flower:

*Diameter* (*fully open*).—60–80 mm.

*Flower shape* (*fully open*).—Top view: round. Side view. Upper portion: flattened. Lower portion: flattened convex.

*Petalage.*—Semi-double (8–19 petals; mean of 12 petals).

*Colour.*—General tonality: 53A. ½ open: deep red 60A. ¾ open: deep red 53A. fully open: deep red/pink, aged 59C and 61C. Central zone of petal, outer surface: 60C. Central zone of petal, inner surface: 53A. Margin of petal, outer surface: 60B. Margin of petal, inner surface: 53A.

*Basal petal spot.*—Outer surface colour: 61C. Inner surface colour: 57A. Size, outer surface: medium. Size, inner surface: large.

*Sepals.*—Upper surface is tomentose (hairy) with small prickles along the margin. Green (RHS 143C) with a few flowers with greyed-purple (RHS 187D). Lower surfaces are yellow-green (RHS 144A) with a few flowers with greyed-purple (RHS 187C). Texture is smooth with small prickles present. Average width at the widest spot along the sepal (near the base) is 8.5 mm.

*Fragrance.*—Weak or absent.

*Lastingness.*—Flowers when cut and placed in tap water, last approximately 7 days under normal laboratory conditions. Flowers generally last 2–3 weeks on the plant depending on soil moisture and fertility as well as environmental conditions (especially wind).

*Bud.*—Average bud size varies with environmental and growing conditions. Floral buds (taken when the sepals are open but prior to petal unfurling) average 26 mm in length; while width averages 15 mm.

Petals:

*Petal length.*—33–44 mm.

*Petal width.*—32–44 mm.

*Shape.*—Orbicular.

*Margin.*—Weak curling of the margin.

*Margin undulation.*—Weak to medium.

*Petaloids.*—Red purple (outside RHS 60A, inside RHS 53A, with white streak RHS 155D), oval in shape and approximately 23 mm in length and 14 mm in width.

Reproductive organs:

*Stamen.*—filament is white with green tinge (RHS 145D) with an average length of 8 mm.

*Anthers.*—Yellow-orange 14B; average length 3 mm.

*Stigmas.*—Inferior to or at the same level relative to the height of the anthers; RHS 162B in color.

*Styles.*—Medium to long styles (average length 5 mm), and yellow-green (RHS 145A) in colouration.

*Receptacle.*—Small, pitcher-shaped, 144A with 187C in colouration. Stamen numbers averaged 106 in a typical flower with pistils averaging 54 per inflorescence.

*Pollen.*—Generally yellow in color (RHS 15A).

*Receptacle.*—Averages 8 mm in length and 8 mm in width; smooth; yellow green in color (RHS 144B).

'Emily Carr' is fertile and seeds are formed on a regular basis. The fruits are seldom selected by wildlife (birds) as a food source. Pollen is viable and this cultivar can be used as a pollen parent in breeding programs.

Resistance to diseases: Resistant to mildew, susceptible to black spot, moderately susceptible to rust.

Resistance to cold: Resistant to −35° C. hardy to zone 3.

I claim:

1. A new and distinct variety of rose plant, substantially as herein shown and described as a distinct and novel rose variety due to its deep red flowers, disease resistance and cold tolerance.

* * * * *

UNITED STATES PATENT AND TRADEMARK OFFICE

CERTIFICATE OF CORRECTION

PATENT NO. : PP 19,873 P3
APPLICATION NO. : 11/880142
DATED : March 31, 2009
INVENTOR(S) : Claude Richer It is certified that error appears in the above-identified patent and that said Letters Patent is hereby corrected as shown below:

In the Specification:

Column 1, line 12, "(Lammert's selection" should be --Lammert's selection--, and "Morden Cardinette)" should be --Morden Cardinette--.

Column 3, line 47, "color" should be --colour--.

Column 4, line 53, "Color" should be --Colour--.

Column 4, line 61, "Color" should be --Colour--.

Column 6, line 22, "color" should be --colour--.

Column 6, line 29, "color" should be --colour--.

Column 6, line 31, "color" should be --colour--.

Signed and Sealed this

Twenty-third Day of June, 2009

John Doll

JOHN DOLL
*Acting Director of the United States Patent and Trademark Office*